United States Patent [19]

Murrell

[11] Patent Number: 4,567,690

[45] Date of Patent: Feb. 4, 1986

[54] SELECTIVELY CLOSED MODULAR CULTIVATION APPARATUS

[76] Inventor: K. Dale Murrell, 1900 Ivy La., P.O. Box 1254, Morristown, Tenn. 37814

[21] Appl. No.: 550,762

[22] Filed: Nov. 10, 1983

[51] Int. Cl.⁴ .............................................. A01G 9/00
[52] U.S. Cl. ........................................ 47/17; 47/14; 47/48.5
[58] Field of Search ............... 47/17, 62, 86, 48.5, 47/26, 14, 19; 52/66, 72; 119/15

[56] References Cited

U.S. PATENT DOCUMENTS

| | | | |
|---|---|---|---|
| 1,993,620 | 3/1935 | Otwell | 47/86 |
| 2,092,155 | 9/1937 | Hackett | 119/15 |
| 3,558,181 | 1/1971 | Peterson | 52/66 |
| 4,115,951 | 9/1978 | Becker et al. | 47/48.5 |
| 4,148,154 | 4/1979 | King | 119/15 |
| 4,163,342 | 8/1979 | Fogg et al. | 47/62 |
| 4,194,320 | 3/1980 | Svirklys | 119/15 |
| 4,265,300 | 5/1981 | Kurimoto | 47/17 |
| 4,316,347 | 2/1982 | Smith | 47/17 |

FOREIGN PATENT DOCUMENTS

91450 4/1958 Norway ........................... 47/26

*Primary Examiner*—Robert A. Hafer
*Assistant Examiner*—Bradley M. Lewis
*Attorney, Agent, or Firm*—Pitts and Brittian

[57] ABSTRACT

A modular cultivation apparatus for the cultivation of plants and the simultaneous production of earthworms and fertilizer/top soil. The apparatus comprises an enclosure (12) including a modular foundation (14) comprising a plurality of plant growth modules (34) for the cultivation of plants and a plurality of harvest modules (36) for the growth and harvest of earthworms. The enclosure (12) further comprises side walls (16) mounted atop and supported by the modular foundation (14), such side walls (16) in turn supporting a roof member (26). In one embodiment, the apparatus further comprises an interior grow light (52), and a self-contained irrigation system (76) for dispersing liquid nutrient or other liquids to the harvest modules (36) and plant growth modules (34).

19 Claims, 9 Drawing Figures

SELECTIVELY CLOSED MODULAR CULTIVATION APPARATUS

DESCRIPTION

1. Technical Field

This invention relates to a selectively closed modular cultivation apparatus for the cultivation of plants and the simultaneous production of earthworms and fertilizer/top soil.

2. Background Art

Soil improvement has been previously described whereby earthworms are seeded into a natural soil to aerate and otherwise enrich such soil, and there has long been a market for earthworms for use as bait by fishermen. Also, previously described, is the method of pouring a liquid nutrient or leaching fluid on natural soil to produce an enriched soil or fertilizer. However, problems arise in the cultivation of plants and the simultaneous production of earthworms and fertilizer/top soil in that the processes necessary to derive the resulting products are often disruptive of one another. For example, the removal of earthworms from an environment in which plants are cultivated may be disruptive of plant growth unless the harvest of the plants and the harvest of the earthworms is done simultaneously. Similarily, removal of the enriched soil from the cultivation environment may be disruptive of both plant growth and earthworm production.

In U.S. Pat. No. 3,654,903 a method for the cultivation of plants and the simultaneous production of earthworms and compost is disclosed. However, it will be noted that in such method earthworm migration is severely limited and in fact the method requires the maintenance of a plurality of individual earthworm communities rather than the more efficient practice of maintaining a large earthworm environment with the capability of selectively harvesting earthworms from locations within the environment. It will be further noted that in the disclosed method of U.S. Pat. No. 3,654,903 the leaching and growing columns must be disassembled in order to harvest the earthworms.

Therefore, an object of the present invention is to provide a selectively closed modular cultivation apparatus for the cultivation of plants and the simultaneous production of earthworms and fertilizer/top soil.

Another object of the present invention is to provide a selectively closed modular cultivation apparatus from which plants or earthworms may be harvested, or fertilizer/top soil removed, without disruption of ongoing processes within the cultivation environment.

Yet another object of the present invention is to provide a controlled ecologically balanced environment for the production of fertilizer/top soil and the cultivation of growing plants and earthworms, and to provide an agricultural study model as a scientific method of improving farming and soil improvement techniques.

A further object of the present invention is to provide a modular cultivation apparatus for processing biodegradable waste material and organic matter to produce top soil.

Another object of the present invention is to provide a selectively closed modular cultivation apparatus which is inexpensive to manufacture and maintain.

DISCLOSURE OF THE INVENTION

Other objects and advantages will be accomplished by the present invention which provides a selectively closed modular cultivation apparatus for the cultivation of plants and the simultaneous production of earthworms and fertilizer/top soil. The apparatus comprises a modular foundation including a plurality of rearrangable plant growth modules for the cultivation of plants and growth of earthworms, and a plurality of rearrangable harvest modules for the growth and harvest of earthworms, such modules being provided with selectively arranged holes to permit the migration of earthworms and liquid nutrient from one module to another module. The apparatus further comprises side walls mounted atop and supported by the modular foundation, and a roof member supported by the side walls. In one embodiment, an interior grow light is provided to aid in plant growth, as well as an irrigation system for dispersing a liquid nutrient or other liquid to the various modules. The apparatus may be selectively closed and sealed to obviate influence from the outside environment and to allow internal pressurization. The rearrangable harvest modules and plant growth modules allow the harvest of either plant life or earthworms, or the removal of fertilizer/top soil without disruption of other ongoing growth processes.

BRIEF DESCRIPTION OF THE DRAWINGS

The above-mentioned features of the present invention will become more clearly understood from the following detailed description read together with the drawings in which.

BEST MODE FOR CARRYING OUT THE INVENTION

A selectively closed modular cultivation apparatus incorporating various features of the present invention is illustrated generally at 10 of the figures. The apparatus 10 is designed to provide a controlled, ecologically balanced environment for the growth and harvest of both plants and earthworms, and for the production of fertilizer/top soil. In the preferred embodiment, all growth medium is sanitized to prevent extraneous bacteria, germs, etc., from being involved in the ecological cycles. In a controlled environment, the growth cycle is continuous. The apparatus 10 generally comprises an enclosure 12 including a modular foundation 14 releasably supporting four planar side walls 16, each of the side walls 16 further comprising an outer wall 18 and an inner wall 20 fixedly secured to one another with stud members 22. The stud members 22 not only serve to support and strength the side walls 16, but also serve to separate outer wall 18 and inner wall 20, thus creating an insulating space 24 (see FIG. 5) to insulate the enclosure 12 from the influence of the outside environment. However, it will be appreciated that the apparatus of the present invention could be accomplished, although at risk of reduced efficieny, using single layer side walls.

Figure 1:
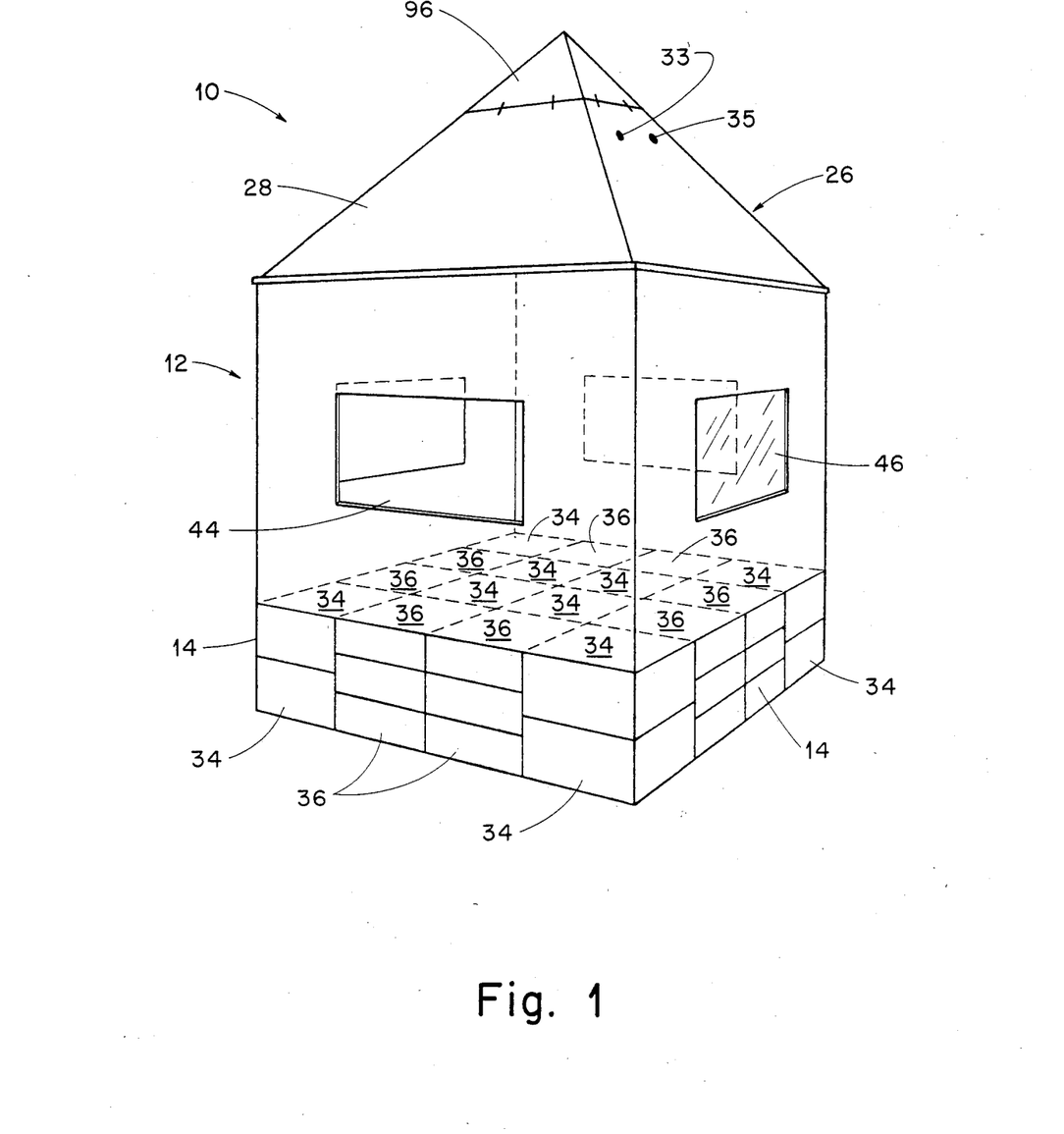
FIG. 1 illustrates a perspective view of the apparatus of the present invention.
Figure 2:
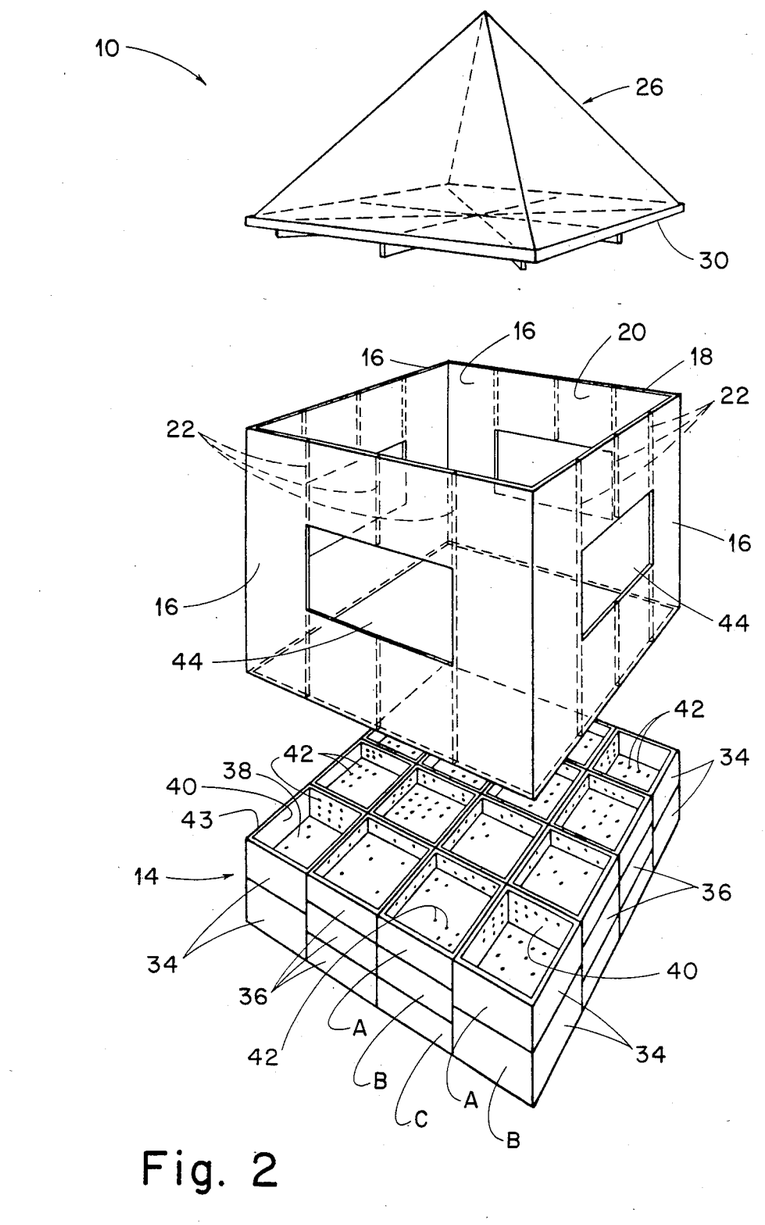
FIG. 2 illustrates an exploded perspective view of the modular cultivation apparatus of the present invention.

The enclosure 12 further comprises a roof member 26 releasably supported by the side walls 16. The roof member 26 integrally comprises a canopy portion 28 and an interior ceiling 30, resultantly defining a fluid impervious reservoir 32 within the roof member 26 (see FIG. 5). As will be discussed in more detail below, the reservoir 32 serves to store a liquid nutrient, water, or other liquid for irrigation of plants within the enclosure 12 and to facilitate leaching of the soil. As is illustrated in FIG. 1, in one embodiment of the apparatus 10, the canopy portion 28 of roof member 26, comprises a removable dome portion 96 to provide access to the reservoir 32 such that fish or other marine life can be added and the reservoir 32 used as an aquarium. It will be further noted in the illustrated embodiment of FIG. 1, that a closable opening 33 is provided to allow the insertion of liquid into the reservoir. Further, an intake valve 35 is provided to allow for the pressurization or depressurization of the interior of the roof member 26 or allow for the insertion or removal of gaseous substances.

Desirably, the enclosure 12 is fabricated of plexiglas or some other durable transparent material, such that light can pass into the enclosure 12 to facilitate plant growth and such that an unrestricted view of the interior of the enclosure 12 is provided. However, it will be appreciated that the enclosure 12 can be fabricated of various durable materials and, although desirable, transparency is not essential to the function of the apparatus 10 given provisions for an internal light source.

More specifically, the foundation 14 comprises a plurality of rearrangable plant growth modules 34 and harvest modules 36 for holding soil or some other growth medium. The plant growth modules 34 are independently subjacently tiered and adjacently contiguous to the harvest modules 36 which are also individually, subjacently tiered. In the illustrated embodiment, the tiers of plant growth modules 34 comprise an upper level A and a lower level B, and the harvest modules 36 comprise descending levels A, B, and C. (For the purpose of clarity, the modules 34 and 36 may be referred to herein using the appropriate numerical designation in conjunction with the alphabetic level designation, e.g., harvest module 36C.) However, it will be noted that the number of levels of the various modules can vary and the illustrated embodiment is simply illustrative of one preferred embodiment.

Each of the modules 34 and 36 comprise a bottom portion 38 and module walls 40. All module walls 40 which are interior with respect to the enclosure 12 are provided with selectively spaced holes 42 registering with holes 42 in the module wall 40 of the adjacent module 34 or 36, such that earthworms are able to migrate horizontally from one module to another. Similarly, all bottom portions 38 which are interior with respect to the enclosure 12, are provided with holes 43 to allow vertical migration of the earthworms and to allow the downward flow of liquid from module to module resulting in a leaching action, in turn, resulting in a concentration of nutrient enriched soil in the lower level modules 34B and 36C.

In the operation of the apparatus 10, plants are seeded, grown and harvested in the plant growth modules 34A. Further, earthworms are introduced into the modules 34A and 34B, which are the breeder areas. After introduction, the earthworms tend to migrate throughout the various modules 34 and 36, distributing more or less evenly throughout the foundation 14. Thus, the earthworms aerate and otherwise enrich the soil throughout the foundation 14 while increasing their numbers through reproduction. The harvest modules 36 are not seeded for plant growth and are reserved for the growth and harvest of earthworms, and the production of fertilizer/top soil. Given the segregated use of the various modules 34 and 36, earthworms can be harvested from the harvest modules 36 without disrupting the plant growth in the upper level plant growth modules 34A and without disrupting the entire earthworm population. Further, biodegradable waste material and organic matter can be introduced into the harvest modules 36 to be processed by the earthworm population into new top soil while simultaneously promoting the growth of the earthworm population. Once again, the top soil produced in the harvest modules 36 may be removed from the apparatus 10 without disruption of the plant growth in the modules 34A, yet the modules 34 continue to benefit from the presence of an earthworm population.

Figure 3:
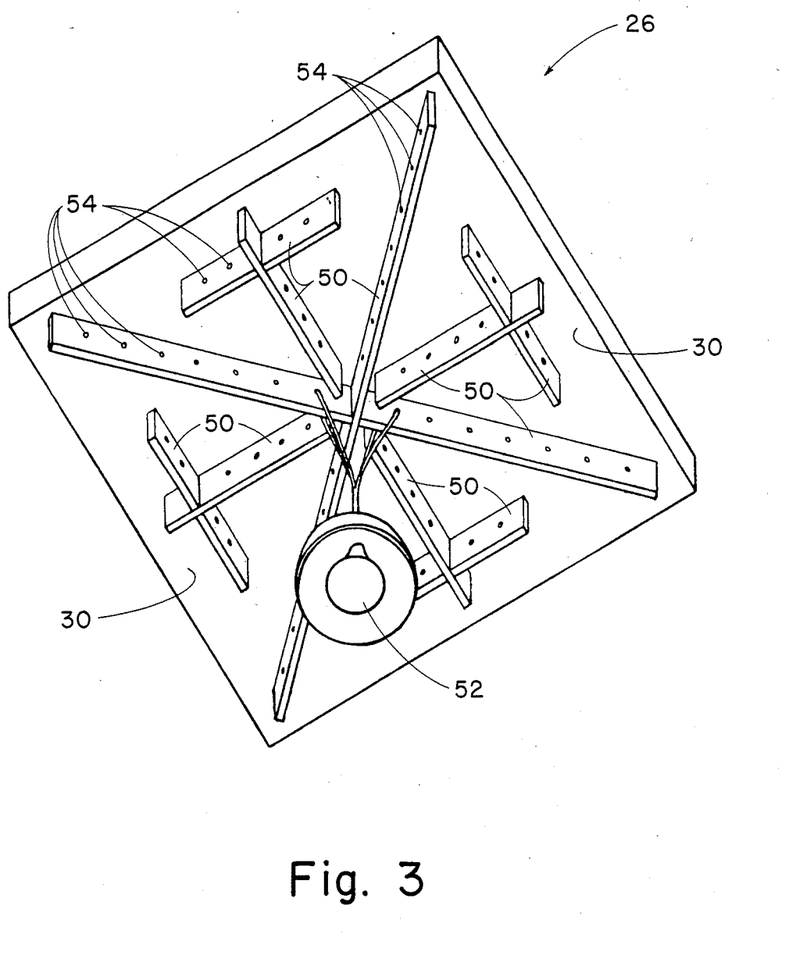
FIG. 3 illustrates a perspective view of the bottom of the roof member of the present invention.

As discussed briefly above, the side walls 16 of enclosure 12 are supported by the outer edge portion of foundation 14. The side walls 16 are provided with openings 44 which may be selectively closed and sealed with door panels 46. The openings 44 allow access to the interior of the enclosure 12 for crop or equipment maintenance. Further, the roof member 26 is releasably mounted on and supported by upper edge portion 48 of the side walls 16. As illustrated in FIG. 3, the interior ceiling 30 of roof member 26 is provided with a plurality of downwardly extending support members 50 for supporting or tying up plants and for supporting the grow light 52. If desired, the support members 50 can be provided with holes 54 to facilitate the tying up of plants or the hanging or mounting of various items of equipment.

Figure 4:
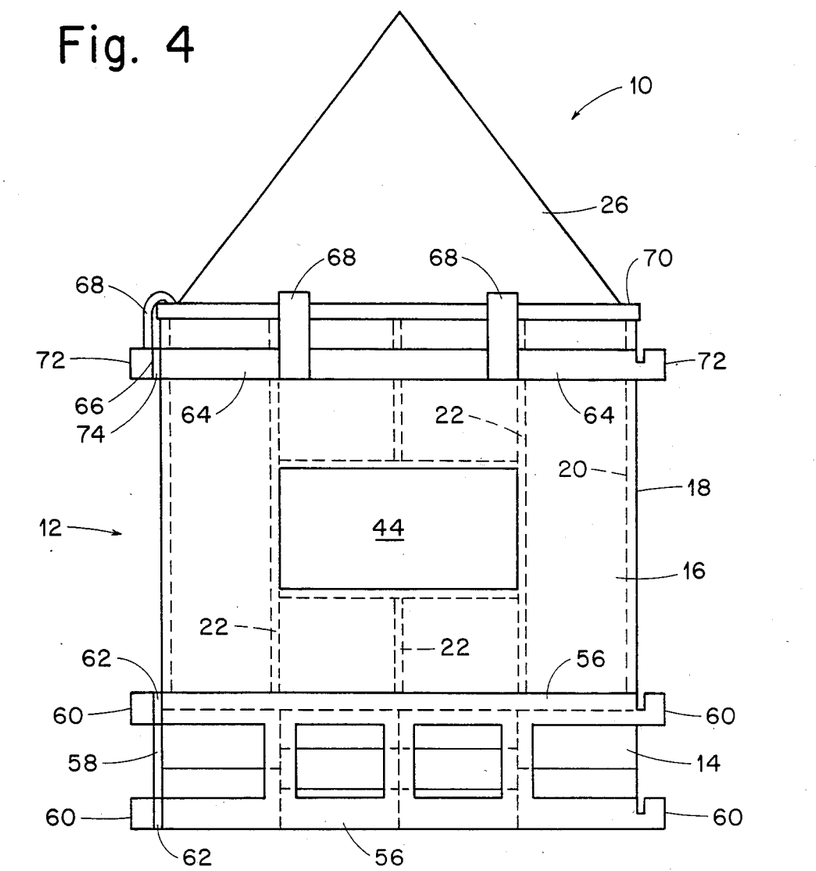
FIG. 4 illustrates a side elevation of the apparatus of the present invention and a means for securing the various components of the apparatus of the present invention.
Figure 4A:
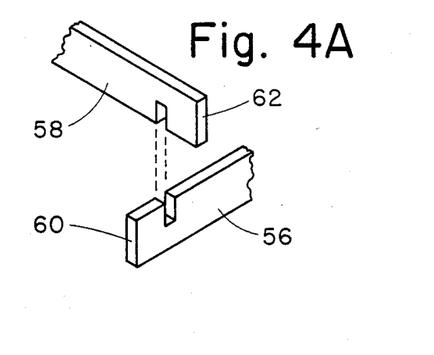
FIG. 4A illustrates a perspective view of a portion of the means for securing the various components of the present invention.
Figure 4B:
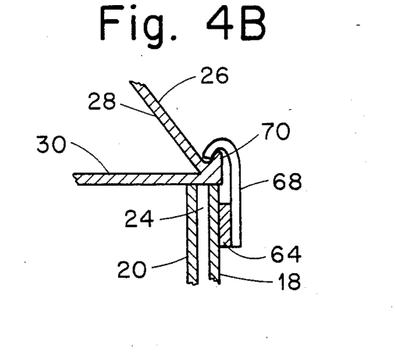
FIG. 4B illustrates a side elevation partially in section, of a brace member of the apparatus of the present invention.

In the illustrated embodiment of FIG. 4, means for securing the various structures of enclosure 12 are provided. These securing means comprise a first pair of side panels 56 and a second pair of side panels 58. The side panels 56 and 58 are designed to secure the modules 34 and 36 in their stacked configuration as well as to maintain the side walls 16 in position upon the foundation 14. The panels 56 and 58 are provided with interlocking end portions 60 and 62, respectively, such that the panels 56 and 58 may be releasably joined to secure the entire perimeter of the foundation 14 and the lower portion of the side walls 16. Also, provided are upper brace members 64 and 66 which serve to secure the roof member 26 in place and to brace the upper portion of the side wall 16. Each of the brace members 64 and 66 are provided with a pair of hook supports 68 extending upwardly from the brace members 64 and 66 to engage the perimeter lip 70 of roof member 26. Further, the brace members 64 and 66 are provided with interlocking end portions 72 and 74, respectively, which, functioning in the same manner as the interlocking end portions 60 and 62, serve to releasably join the brace members 64 and 66. It will be appreciated that while the above described securing means provide for easy assembly and disassembly of the apparatus 10 and provide a degree of portability, various other securing means can be used to insure that the various structures are secured in position, and the described embodiment is simply illustrative of one such means.

Figure 5:
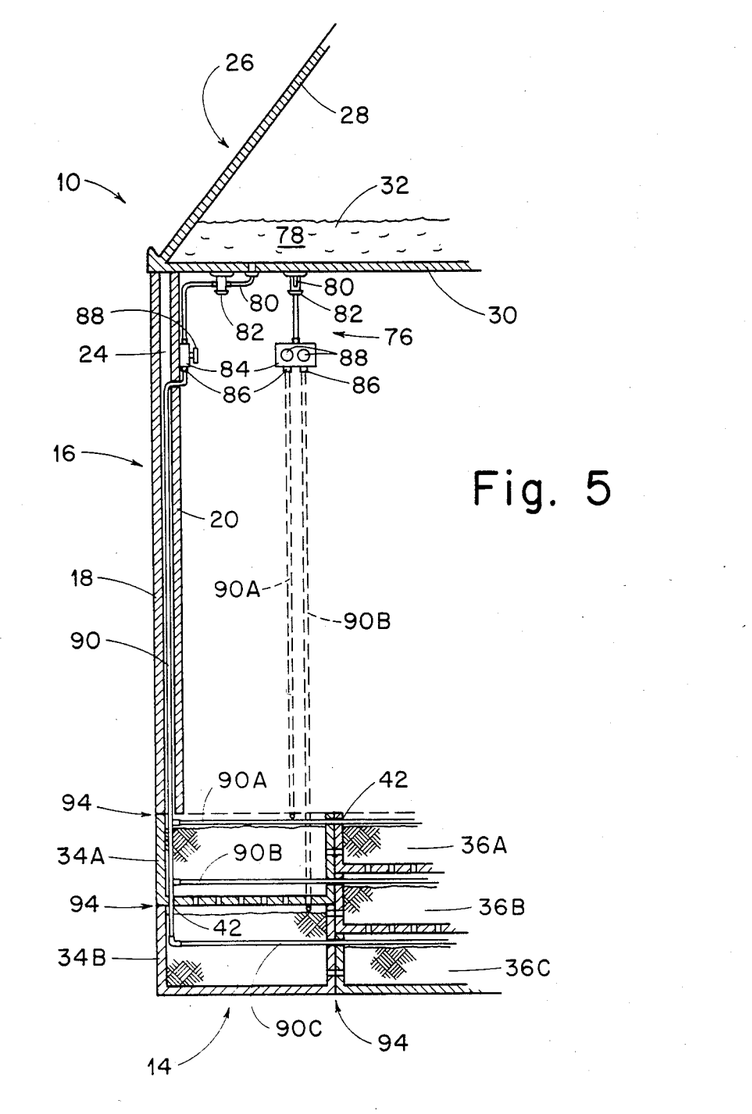
FIG. 5 is a side elevation, partially in section, of the irrigation system of the apparatus of the present invention.
Figure 6:
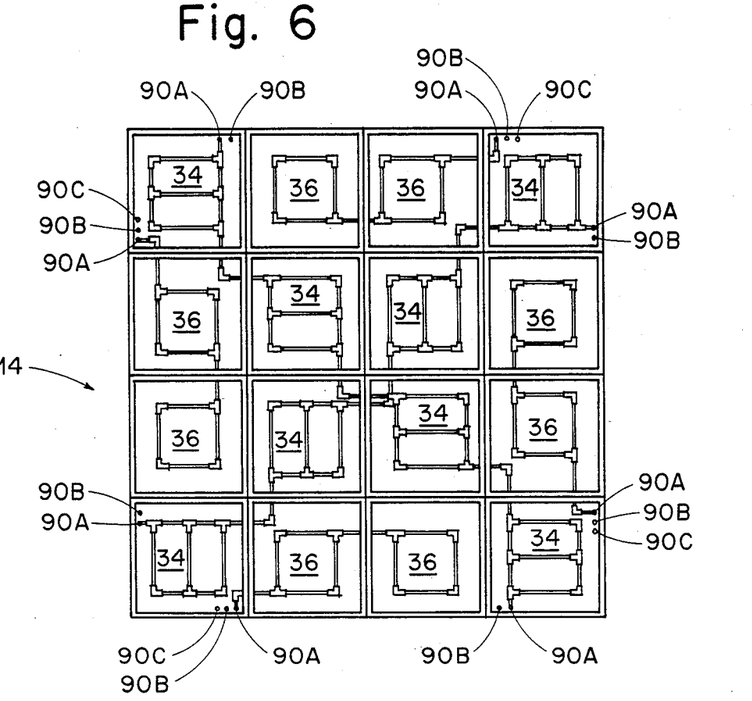
FIG. 6 illustrates a top view of a portion of the irrigation system of the present invention.
Figure 7:
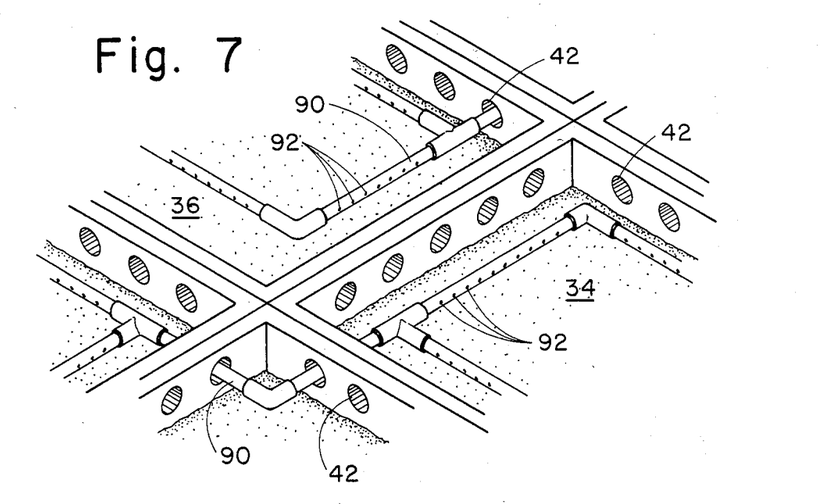
FIG. 7 illustrates a perspective view of a portion of the irrigation system of the present invention.

As illustrated in FIGS. 5, 6, and 7, one embodiment of the apparatus 10 is provided with an irrigation system 76. The irrigation system 76 comprises the reservoir 32 for holding a liquid 78 such as a liquid nutrient or some other liquid to be dispersed in or on the soil of the modules 34 and 36. From the reservoir 32, the liquid 78 is routed through the irrigation pipes 80 to the main cut off valves 82 mounted on the interior ceiling 30 which allows the flow of liquid to be selectively shut off. From the main valves 82, the liquid 78 is routed through the pipes 81 to the multiple output feeder valves 84 mounted on interior walls 20 of side walls 16. the feeder valves 84 are provided with multiple output conduits 86, each provided with its own flow control means 88, for selectively controlling the volume of liquid 78 passing through the conduit 86. It will be noted that in the illustrated embodiment, the feeder valves 84 supplying the modules 34, are provided with two output conduits 86 corresponding to the module levels A and B, and the feeder valves 84 supplying the modules 36 are provided with three output conduits 86 corresponding to module levels A, B and C. From the conduits 86 of the feeder valves 84, the liquid 78 is routed to the various modules 34 and 36 of levels A, B and C, through module feeder lines 90 in turn routed through the insulation space 24 of side walls 16.

As the feeder lines 90 reach the various module levels A, B and C, they are routed through the holes 42 in modules 34 and 36 to various locations throughout the foundation 14. As illustrated in FIG. 6, the feeder lines 90 are provided with selectively disposed dispersing holes 92 for releasing the liquid 78 onto or into the soil within the modules 34 and 36. Further, as illustrated in FIG. 6, the feeder lines 90 as they are routed through holes 42 can be arranged in various geometric configurations to insure thorough dispersion of the liquid 78 throughout the foundation 14. While the illustrated embodiment discloses one suitable irrigation means, the apparatus 10 can be easily adapted to utilize various other irrigation means if desired. It will also be noted that given the vertical stacking of the various modules 34 and 36, when a liquid nutrient or other liquid is dispersed on the modules 34 and 36, a leaching action results with a resultant improvement or enrichment in the lower level modules 34 and 36. With respect to the modules 34, the soil from the lower level B can be used to grow the next crop subsequent to the harvest of the crops grown in level A. Thus, as one crop is being grown, the soil for a subsequent crop is being prepared by the leaching action and by the earthworms. Likewise, the soil in the lower level modules 36 is improved by both leaching and by the earthworm population and may be removed and used as desired.

The apparatus 10 is designed such that it provides, if desired, a closed environment with an internal light source and an internal source of liquid nutrient or other liquid. If desired, temperature controlling or modifying apparatus can be incorporated to make the apparatus 10 closed to the influence of the outside environment for extended periods of time. Further, it will be recognized by those skilled in the art that with the addition of pressure seals at the locations 94, the enclosure 12 may be pressurized for experimental use or for use in an environment lacking the necessary atmospheric pressure. This makes the apparatus 10 ideal for experimentation in the field of cultivating plants above and beyond its capacity to function as a food producing unit. Whether used as a closed or open system, the apparatus 10 provides a desirable environment for the cultivation of plant life and for the growth of earthworms, while at the same time producing fertilizer/top soil as a by-product.

While a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. A modular cultivation apparatus for the cultivation of plants and the simultaneous production of earthworms and fertilizer/top soil, said apparatus comprising:
    a modular foundation defining a perimeter having a top edge, said modular foundation comprising a first plurality of tiered rearrangeable modules for holding soil or some other growth medium for the cultivation of said plants and a second plurality of tiered rearrangable modules for the production of said earthworms and said fertilizer/top soil, said second plurality of modules adjacently contiguous said first plurality of modules, each of said module of said first and second plurality comprising an independent bottom portion and side wall portions to form trays, said bottom portion and said side wall portions of said modules which are internal to said apparatus being provided with a plurality of selectively arranged and aligned holes to permit the migration of said earthworms between said first plurality of modules and said second plurality of modules; and
    an enclosure releasably supported on said top edge of said modular foundation.

2. A cultivation apparatus of claim 1 wherein said enclosure comprises side walls releasably mounted atop and supported by said top edge of said foundation; and a canopy member releasably mounted on a top edge of said side walls, said side walls defining an enclosure perimeter corresponding to said perimeter of said foundation.

3. The cultivation apparatus of claim 2 wherein said side walls comprise an outer wall and an inner wall separated by and secured to a plurality of supporting stud members so as to define an insulation space between said outer wall and said inner wall.

4. The cultivation apparatus of claim 2 wherein said side walls are provided with at least one opening for providing access to the interior of said enclosure, said opening being provided with a door panel for selectively closing said opening.

5. The cultivation apparatus of claim 2 wherein said canopy member comprises a roof member and an interior ceiling member defining a fluid impervious reservoir within said roof member, said roof member being provided with at least one closable opening to facilitate the filling of said reservoir with a fluid.

6. The cultivation apparatus of claim 5 wherein said roof member further comprises a removable dome member for providing access to the interior of said reservoir.

7. The cultivation apparatus of claim 1 wherein said apparatus further comprises a grow light mounted within said enclosure to promote plant growth.

8. The cultivation apparatus of claim 5 wherein said canopy member further comprises a plurality of downwardly extending support members mounted on said interior ceiling member for supporting or tying up said plants or for supporting equipment within said enclosure.

9. The cultivation apparatus of claim 1 wherein said apparatus is provided with an irrigation system for providing liquid nutrients or other liquids to said first and second plurality of modules.

10. The cultivation apparatus of claim 9 wherein said irrigation system comprises a reservoir for releasably holding said liquid nutrient or other liquid, and further comprising, a pipe system connected at a first end to said reservoir for carrying said liquid nutrient or other liquid to selected locations within said apparatus, said pipe system being provided with sections of pipe provide with selectively disposed holes for dispersing said liquid nutrient or other liquid, said irrigation system further comprising at least one feeder valve for regulating the rate at which said liquid nutrient or other liquid is released from said reservoir and dispersed to said modules.

11. The cultivation apparatus of claim 2 wherein said apparatus further comprises a plurality of side panels, equal in number to said side walls, each provided with interlocking end portions for releasably locking said side panels about said perimeter of said modular foundation and about said perimeter of said enclosure at said top edge of said foundation to secure the relative position of said foundation and said side walls; and a plurality of brace members, equal in number to said side walls, each provided with interlocking end portions for locking said brace members about said perimeter of said side walls of said enclosure, each of said brace members being provided with at least one hook support extending upwarding from said brace member to engage said canopy member and hold said canopy member against said top edge of said side walls.

12. A modular cultivation apparatus for the cultivation of plants and the simultaneous production of earthworms and fertilizer/top soil, said apparatus comprising:

a modular foundation defining a perimeter having a top edge including a plurality of plant growth modules for the cultivation of said plants and the growth of said earthworms, and a plurality of harvest modules for the growth and harvest of said earthworms, each said harvest module and each said plant growth module having an individual bottom portion and side wall portions, said bottom portion and said side wall portions of said plant growth modules and said harvest modules which are internal with respect to said foundation being provided with a plurality of selectively arranged and aligned holes to permit the migration of said earthworms between said plant growth modules said harvest modules, said plant growth modules being arranged such that said plant growth modules are individually subjacently tiered and adjacently contiguous to said harvest modules, and said harvest modules are arranged such that said harvest modules are individually subjacently tiered, said plant growth modules and said harvest modules adapted for individual removal from said modular foundation;

side walls for forming sides at an enclosure defining a perimeter mounted atop and supported by said modular foundation, said side walls each having an outer wall and an inner wall separated by and secured to a plurality of supporting stud members so as to define an insulation space between said outer wall and said inner wall; said side walls being provided with at least one opening for providing access to the interior of said enclosure, said opening being provided with a panel for selectively closing said opening; and a roof member releasably supported by said side walls, said roof member comprising a canopy portion and an interior ceiling defining a fluid impervious reservoir within said roof member, said roof member being further provided with at least one closeable opening to facilitate the filling of said reservoir with a fluid, said interior ceiling being provided with a plurality of downwardly extending support members for supporting or tying up said plants and for supporting various equipment.

13. The cultivation apparatus of claim 12 wherein said apparatus further comprises an irrigation system for providing liquid to said harvest modules and said plant growth modules, said irrigation system comprising said reservoir defined within said roof member; and at least one irrigation pipe connected at a first end to said reservoir and connected at a second end to a feeder valve provided with a plurality of output conduits, each said output conduits being provided with flow control means for regulating the flow of liquid through said conduits, each said output conduits being further provided with a feeder line for carrying said liquid to said plant growth modules and said harvest modules, said feeder lines being provided with selectively disposed holes for dispersing said liquid.

14. The cultivation apparatus of claim 13 wherein said irrigation pipe is provided with a main cut off valve for regulating the flow of said from said reservoir liquid to said feeder valve.

15. The cultivation apparatus of claim 12 wherein said apparatus further comprises a grow light releasably supported by said support members of said ceiling in order to promote plant growth.

16. The cultivation apparatus of claim 12 wherein said apparatus further comprises a plurality of side panels, equal in number to said side walls, each provided with interlocking end portions for releasably locking said side panels about said perimeter of said modular foundation and about said enclosure perimeter at a lower portion of said side walls to secure the relative position of said foundation and said side walls; and a plurality of brace members, equal in number to said side walls, each provided with interlocking end portions for locking said brace members about an upper portion of said perimeter of said side walls, each of said brace members being provided with at least one hook support extending upwardly from said brace member to engage said roof member in order to hold said roof member in place against said side walls.

17. The cultivation apparatus of claim 12 wherein said canopy portion of said roof member further comprises a removable dome member for providing access to the interior of said reservoir.

18. The cultivation apparatus of claim 12 wherein said apparatus is provided with a plurality of fluid impervious seals between junctures of said modular foundation, said side walls and said roof member, to facilitate pressurization of said apparatus relative to external pressure.

19. The cultivation apparatus of claim 12 wherein said tier of plant growth modules contains two modules, and said tiers of harvest modules contains three modules.

* * * * *